US005696138A

United States Patent [19]
Olesen et al.

[11] Patent Number: 5,696,138
[45] Date of Patent: Dec. 9, 1997

[54] UREA DERIVATIVES AND THEIR USE

[75] Inventors: Søren-Peter Olesen, Klampenborg; Peter Moldt, Humlebaek; Ove Pedersen, Ringsted, all of Denmark

[73] Assignee: NeuroSearch A/S, Glostrup, Denmark

[21] Appl. No.: 535,267

[22] PCT Filed: Mar. 30, 1994

[86] PCT No.: PCT/EP94/01008

§ 371 Date: Dec. 27, 1995

§ 102(e) Date: Dec. 27, 1995

[87] PCT Pub. No.: WO94/22807

PCT Pub. Date: Oct. 13, 1994

[30] Foreign Application Priority Data

Apr. 7, 1993 [DK] Denmark ................................. 0411/93

[51] Int. Cl.$^6$ ................. C07D 213/36; C07C 233/29; A61K 31/165

[52] U.S. Cl. ................. 514/349; 514/345; 514/585; 514/598; 514/617; 514/631; 514/634; 546/297; 546/298; 546/360; 564/28; 564/52; 564/170; 564/237; 564/247

[58] Field of Search ................. 546/297, 298, 546/360; 564/28, 52, 170, 237, 247; 514/345, 349, 585, 598, 617, 631, 634

[56] References Cited

U.S. PATENT DOCUMENTS

| | | | |
|---|---|---|---|
| 3,331,874 | 7/1967 | Stecker | 564/52 |
| 3,689,550 | 9/1972 | Schellenbaum et al. | 514/598 |
| 3,935,262 | 1/1976 | Lestina et al. | 260/559 R |

FOREIGN PATENT DOCUMENTS

| | | |
|---|---|---|
| 0354553 | 2/1990 | European Pat. Off. |
| 0477819 | 4/1992 | European Pat. Off. |
| 1912553 | 10/1969 | Germany |
| 2260203 | 6/1973 | Germany |

OTHER PUBLICATIONS

Mohsen, A. et al., "Synthesis and Evaluation of Novel N–Substituted N'–(3–Hydroxy–17–oxoestra–1,3,5(10)–trien–2–and –4–yl)thiourea Derivatives for Binding to the Estrogen Receptor and Cytotoxic Activity on MCF–7 Cells", Journal of Pharmaceutical Sciences, 73 (12), 1984, pp. 1871–1873.

Yamana, T., et al., "Stabilization of Drugs. I. The Quantitative Prediction of the pH–Dependency of Amide and Anilide Hydrolyses By Neighboring Hydroxyl Groups", Chem. Pharm. Bull., 21 (4), 1973, pp. 721–728.

European Search Report, Aug. 18, 1994.

Gandolfo, G., et al., "K+ channel openers descrease seizures in genetically epileptic rats", European Journal of Pharmacology, 167 (1989) pp. 181–183.

Abele, A., et al., "Potassium Channel Activators Abolish Excitotoxicity in Cultured Hippocampal Pyramidal Neurons", Neuroscience Letters, 115 (1990) pp. 195–200.

Ben–Ari, Y., et al., "Activators of ATP–Sensitive K+ Channels Reduce Anoxic Depolarization in CA3 Hippocampal Neurons", Neuroscience, 37 (1) (1990) pp. 55–60.

Grover, G., et al., "Anti–Ischemic Effects of the Potassium Channel Activators Pinacidil and Cromakalim and the Reversal of these Effects with the Potassium Channel Blocker Glybudrie", The Journal of Pharmacology and Experimental Therapeutics, 251(1) (1989) pp. 98–104.

Williams, A., et al., "Attenuation of Nocturnal Asthma by Cromakalim", The Lancet, 336 (1990) pp. 334–336.

Latorre, R., et al. "Varieties of Calcium–Activated Potassium Channels", Annu. Rev. Physiol., 51 (1989) pp. 385–399.

Brayden, J., et al., "Regulation of Arterial Tone by Activation of Calcium–Dependent Potassium Channels", Science, 256 (1992) pp. 532–535.

Jones, T., et al., "Selective Inhibition of Relaxation of Guinea–Pig Trachea by Charybdotoxin, a Potent Ca++–Activated K+ Channel Inhibitor", J. Pharmacol. Exp. Ther., 255 (1990) pp. 697–706.

Robitaille, R., et al., "Presynaptic Calcium Signals and Transmitter Release Are Modulated by Calcium–Activated Potassium Channels", J. Neurosci, 2 (1) (1992) pp. 297–305.

Suarez–Kurtz, G., et al., "Charybdotoxin and Iberiotoxin on the Spontaneous Tonus of Different Guinea Pig Smooth Muscle", J. Pharmacol. Exp. Ther., 259 (1991) pp. 439–443.

*Primary Examiner*—Zinna Northington Davis
*Attorney, Agent, or Firm*—The Firm of Gordon W. Hueschen

[57] ABSTRACT

A compound having the formula or a pharmaceutically acceptable salt thereof, wherein X, Z, Y, A, D, E, F, $R^1$, $R^2$, $R^3$, $R^4$, $R^{11}$, $R^{12}$ have the meanings set forth in the specification, pharmaceutical compositions comprising the same, and a method of treating therewith.

The compounds are useful as potassium channel openers.

8 Claims, No Drawings

UREA DERIVATIVES AND THEIR USE

The present application is a U.S. national application filed under 35 USC 371 of PCT/EP/94/01008, filed Mar. 30, 1994, which in turn is based upon the priority of Danish application 0411/93, filed Apr. 7, 1995.

The present invention relates to novel urea derivatives, a method of preparing the same, a method of treatment with the novel urea derivatives, and to pharmaceutical compositions comprising the same.

OBJECT OF THE INVENTION

It is an object of the present invention to provide novel urea compounds which are useful in the treatment of disorders or diseases of a living animal body, including a human, and especially in the treatment of disorders or diseases which can be treated by opening cell membrane potassium channels of such a living animal body.

Another object of the present invention is to provide a method of treating disorders or diseases of a living animal body, including a human, which disorders or diseases are responsive to opening of potassium channels and which comprises administering to such a living animal body in need thereof a compound of the invention.

A third object of the present invention is to provide novel pharmaceutical compositions for the treatment of disorders or diseases of a living animal body, including a human, which disorders or diseases are responsive to the opening of potassium channels.

Other objects will be apparent to the person skilled in the art hereinafter.

BACKGROUND OF THE INVENTION

European patent application Publication No 477 819 discloses that certain compounds are openers of BK channels.

It is generally well known that opening of potassium ($K^+$) channels leads to a hyperpolarization and relaxation of cells. The presently known $K^+$ channel openers (e.g. cromakalim and pinacidil) exert their effect primarily by interaction with the $K^+$ channel subtype $K_{ATP}$. These compounds have a high affinity for vascular smooth muscle cells and are thus mostly vasodilators. Recent studies indicate, however, that $K^+$ channel openers hyperpolarizing neuronal cells also have anticonvulsive and antiischemic effects in the central nervous system (the CNS), European Journal of Pharmacology 167, 181–183 (1989), Neuroscience Letters 115, 195–200 (1990), Neuroscience 37(1), 55–60 (1990), The Journal of Pharmacology and Experimental Therapeutics 251(1), 98–104 (1989). Furthermore recent studies demonstrate that potassium channel openers acting on airways smooth muscle (tracheal smooth muscle) cells will have anti-asthmatic effects (Williams et al., The Lancet 336, 334–336 (1990)).

There exist other $K^+$ channel sybtypes than $K_{ATP}$, and one such subtype is the BK channel, also called the maxi-K channel or large-conductance $Ca^{2+}$ dependent $K^+$ channel. The BK channel is present in many cells including most central and peripheral nerve cells, striated muscle cells, smooth muscle cells of the airways, the vasculature, the gastrointestinal tract and bladder, in endo- and exocrine glands including pancreatic β-cells and in kidney tubules (R. Latorre et al., Annu. Rev. Physiol. 51, 385 (1989)).

A scorpion toxin peptide, charybdotoxin, which blocks the BK channel fairly specific has been used to demonstrate that the BK channel plays an important role as a relaxing negative feed-back when the cells in these tissues become highly active or spastic (J. E. Brayden and M. T. Nelson, Science 256, 532 (1992); T. R. Jones et al., J. Pharmacol. Exp. Thor. 255, 697 (1990); R. Robiteille and M. P. Charlton, J. Neurosci. 12, 297 (1992); G. Suarez-Kurtz et al., J. Pharmacol. Exp. Ther. 259, (1991)).

SUMMARY OF THE INVENTION

The invention then, inter alia, comprises the following, alone or in combination:

A compound having the formula

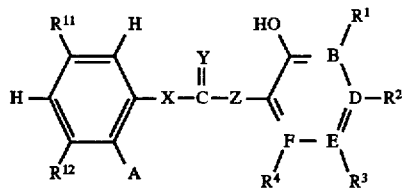

or a pharmaceutically acceptable salt thereof,
wherein

X and Z each independently are NH or CH2, at least one of X and Z being NH;

Y is O, S, NCN, or NH;

B,D,E and F each independently are C or N, at least three of B, D, E, and F being C;

$R^1$ and $R^4$ each independently are hydrogen, halogen, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy;

$R^2$ is hydrogen, $CF_3$, COOH, COO-alkyl, COO-aryl, CO-amino, CN, alkoxy, hydroxy, hydroxymethyl, sulphamoyl, aryloxy, alkylcarbonyl, arylcarbonyl, arylcarbonyloxy, alkylcarbonyloxy;

$R^3$ is hydrogen, halogen, COOH, COO-alkyl, COO-aryl, CO-amino, CN, alkoxy, hydroxy, nitro, hydroxymethyl, sulphamoyl, amino, aryloxy, alkylcarbonyl, arylcarbonyl, arylcarbonyloxy, alkylcarbonyloxy; or $R^2$ and $R^3$ or $R^3$ and $R^4$ together with the carbon atoms to which they are attached form an additional fused carbocyclic ring which may be fully or partially unsaturated;

at least one of $R^{11}$ and $R^{12}$ is halogen, $OCF_3$, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy and the other of $R^{11}$ and $R^{12}$ is hydrogen, halogen, $OCF_3$, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy;

A is hydrogen or together with $R^{12}$ and the carbon atoms to which they are attached form an additional fused carbocyclic ring which may be fully or partially unsaturated, and a compound as above which is N-(2-hydroxy-5-chlorophenyl)-3-(trifluoromethyl) phenylacetic amide, N-(3-(trifluoromethoxy)phenyl)-N'-(2-hydroxy-5-chlorophenyl) urea, N-(3-(trifluoromethyl)phenyl)-N'-(2-hydroxyphenyl) urea, N-(3-(trifluoromethyl)phenyl)-N'-(2-hydroxy-6-nitrophenyl) urea, N-(3-(trifluoromethyl)phenyl)-2-hydroxy-5-chlorophenylacetic amide, N-(3-(trifluoromethyl)phenyl)-N'-(2-hydroxy-5-chlorophenyl) thiourea, N-(3-(trifluoromethyl)phenyl)-N'-(2-hydroxy-5-methoxycarbonylphenyl) urea, N-(3-(trifluoromethyl)phenyl)-N'-(2-hydroxy-4-methoxycarbonyl-5-chlorophenyl) urea, N-(3-(trifluoromethyl)phenyl)-N'-(2-hydroxy-4-methoxcarbonylphenyl) urea, N-(3-(trifluoromethyl)phenyl)-N'-(2-hydroxy-4-chlorophenyl) urea, N-(3-(trifluoromethyl)phenyl)-N'-(2-hydroxy-6-methoxy-3-pyridyl) urea, N-(3-(trifluoromethyl)phenyl)-N'-(2-hydroxy-5-chloro-3-pyridyl) urea, N-(3-(trifluoromethyl)phenyl)-N'-(2-hydroxy-3-nitrophenyl) urea, N-(3-(trifluoromethyl)phenyl)-N'-(2-hydroxy-4-methoxyphenyl) urea, N-(3-(trifluoromethyl)phenyl)-N'-(2, 4-dihydroxyphenyl) urea, N-(3-(trifluoromethyl)phenyl)-N'-(2-hydroxy-5-nitrophenyl) urea, N-(3-(trifluoromethyl)phenyl)-N'-(3-hydroxy-2-naphthyl) urea, N-(3-(trifluoromethyl)phenyl)-N'-(3-hydroxy-2-pyridyl) urea, N-(3-(trifluoromethyl)phenyl)-N'-(2-hydroxy-1-naphthyl) urea, N-(3-(trifluoromethyl)phenyl)-N'-(2-hydroxy-5-chlorophenyl) urea, N-(3-(trifluoromethyl)phenyl)-N'-(2-hydroxy-5-methoxyphenyl) urea, N-(3-(trifluoromethyl)phenyl)-N'-(2-hydroxy-4-(phenylamino)phenyl) urea, N-(3-(trifluoromethyl)phenyl)-N'-(2, 5-dihydroxyphenyl) urea, N-(3-benzoylphenyl)-N'-(2-hydroxy-5-chlorophenyl) urea, N-(3-carbamoylphenyl)-N'-(2-hydroxy-5-chlorophenyl) urea, N-(3-carboxyphenyl)-N'-(2-hydroxy-5-chlorophenyl) urea, N-(3-hydroxyphenyl)-N'-(2-hydroxy-5-chlorophenyl) urea, N-(3-methoxycarbonylphenyl)-N'-(2-hydroxy-5-chlorophenyl) urea, N-(3-methylphenyl)-N'-(2-hydroxy-5-chlorophenyl) urea, or N-(3-nitrophenyl)-N'-(2-hydroxy-5-chlorophenyl) urea, or a pharmaceutically acceptable salt thereof, and wherein a pharmaceutical composition comprising a therapeutically effective amount of a compound as any above together with at least one pharmaceutically acceptable carrier, and a method of treating a disorder or disease of a living animal body, including a human, which disorder or disease is responsive to opening of potassium channels and which comprises administering to such a living animal body, including a human in need thereof an effective amount of a compound having the formula

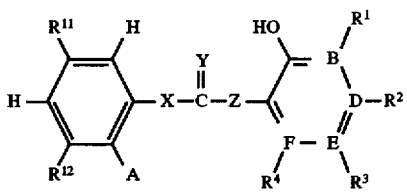

or a pharmaceutically acceptable salt thereof,
wherein

X and Z each independently are NH or CH2, at least one of X and Z being NH;

Y is O, S, NCN, or NH;

B,D,E and F each independently are C or N, at least three of B, D, E, and F being C;

$R^1$ and $R^4$ each independently are hydrogen, halogen, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy;

$R^2$ is hydrogen, halogen, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy;

$R^3$ is hydrogen, halogen, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy; or $R^2$ and $R^3$ or $R^3$ and $R^4$ together with the carbon atoms to which they are attached form an additional fused carbocyclic ring which may be fully or partially unsaturated;

at least one of $R_{11}$ and $R_{12}$ is halogen, $OCF_3$, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy and the other of $R_{11}$ and $R_{12}$ is hydrogen, halogen, $OCF_3$, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy;

A is hydrogen or together with $R^{12}$ and the carbon atoms to which they are attached form an additional fused carbocyclic ring which may be fully or partially unsaturated, and the method as above wherein arterial hypertension, coronary artery spasms, asthma, irritable bowl syndrome, spastic bladder, ischemia, psychosis, or convulsions are treated, and the method as any above wherein the compound is administered in the form of a pharmaceutical composition thereof, in which it is present together with a pharmaceutically acceptable carrier or diluent, and the method as any above wherein N-(1-naphthyl)-N'-(2-hydroxy-5-(trifluoromethyl)phenyl) urea, N-(2-hydroxy-5-chlorophenyl)-3-(trifluoromethyl) phenylacetic amide, N-(3, 5-dichlorophenyl)-N'-(2-hydroxy-5-(trifluoromethyl) phenyl) urea, N-(3-(trifluoromethoxy)phenyl)-N'-(2-hydroxy-5-chlorophenyl) urea, N-(3-(trifluoromethyl)phenyl)-N'-(2-hydroxyphenyl) urea, N-(3-(trifluoromethyl)phenyl)-N'-(2-hydroxy-6-nitrophenyl) urea, N-(3-(trifluoromethyl)phenyl)-N'-(2-hydroxy-5-(trifluoromethyl)phenyl) thiourea, N-(3-(trifluoromethyl)phenyl)-2-hydroxy-5-chlorophenylacetic amide, N-(3-(trifluoromethyl)phenyl)-N'-(2-hydroxy-5-chlorophenyl) thiourea, N-(3-(trifluoromethyl)phenyl)-N'-(2-hydroxy-5-methoxycarbonylphenyl) urea, N-(3-(trifluoromethyl)phenyl)-N'-(2-hydroxy-4-nitro-5-carboxyphenyl) urea, N-(3-(trifluoromethyl)phenyl)-N'-(2-hydroxy-4-nitro-5-methoxycarbonylphenyl) urea, N-(3-(trifluoromethyl)phenyl)-N'-(2-hydroxy-4-methoxycarbonyl-5-chlorophenyl) urea, N-(3-(trifluoromethyl)phenyl)-N'-(2-hydroxy-4-methoxcarbonylphenyl) urea, N-(3-(trifluoromethyl)phenyl)-N'-(2-hydroxy-4-chlorophenyl) urea, N-(3-(trifluoromethyl)phenyl)-N'-(2-hydroxy-6-methoxy-3-pyridyl) urea, N-(3-(trifluoromethyl)phenyl)-N'-(2-hydroxy-5-chloro-3-pyridyl) urea, N-(3-(trifluoromethyl)phenyl)-N'-(2-hydroxy-3-nitrophenyl) urea, wherein X and Z each independently are NH or CH2, at least one of X and Z being NH;

Y is O, S, NCN, or NH;

B,D,E and F each independently are C or N, at least three of B, D, E, and F being C;

$R^1$ and $R^4$ each independently are hydrogen, halogen, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy;

$R^2$ is hydrogen, halogen, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy;

$R^3$ is hydrogen, halogen, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy; or $R^2$ and $R^3$ or $R^3$ and $R^4$ together with the carbon atoms to which they are attached form an additional fused carbocyclic ring which may be fully or partially unsaturated;

at least one of $R^{11}$ and $R^{12}$ is halogen, $OCF_3$, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy and the other of $R^{11}$ and $R^{12}$ is hydrogen, halogen, $OCF_3$, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy;

A is hydrogen or together with $R^{12}$ and the carbon atoms to which they are attached form an additional fused carbocyclic ring which may be fully or partially unsaturated, for the manufacture of a medicament for the treatment of a disorder or disease of a living animal body, including a human, which disorder or disease is responsive to opening of potassium channels, and the use of a compound having the formula

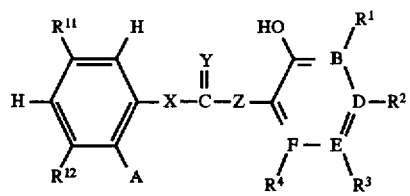

or a pharmaceutically acceptable salt thereof,
wherein

X and Z each independently are NH or CH2, at least one of X and Z being NH;

Y is O, S, NCN, or NH;

B,D,E and F each independently are C or N, at least three of B, D, E, and F being C;

$R^1$ and $R^4$ each independently are hydrogen, halogen, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy;

$R^2$ is hydrogen, halogen, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy;

$R^3$ is hydrogen, halogen, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy; or $R^2$ and $R^3$ or $R^3$ and $R^4$ together with the carbon atoms to which they are attached form an additional fused carbocyclic ring which may be fully or partially unsaturated;

at least one of $R^{11}$ and $R^{12}$ is halogen, $OCF_3$, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy and the other of $R^{11}$ and $R^{12}$ is hydrogen, halogen, $OCF_3$, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy;

A is hydrogen or together with $R^{12}$ and the carbon atoms to which they are attached form an additional fused carbocyclic ring which may be fully or partially unsaturated, for the manufacture of a medicament for the treatment of arterial hypertension, coronary artery spasms, asthma, irritable bowl syndrome, spastic bladder, ischemia, psychosis, or convulsions, and the use as above wherein the compound employed is N-(1-naphthyl)-N'-(2-hydroxy-5-(trifluorom ethyl)phenyl) urea, N-(2-hydroxy-5-chlorophenyl)-3-(trifluoromethyl) phenylacetic amide, N-(3,5-dichlorophenyl)-N'-(2-hydroxy-5-(trifluoromethyl) phenyl) urea, N-(3-(trifluoromethoxy)phenyl)-N'-(2-hydroxy-5-chlorophenyl) urea, N-(3-(trifluoromethyl)phenyl)-N'-(2-hydroxyphenyl) urea, N-(3-(trifluoromethyl)phenyl)-N'-(2-hydroxy-6-nitrophenyl) urea, N-(3-(trifluoromethyl)phenyl)-N'-(2-hydroxy-5-(trifluoromethyl)phenyl) thiourea, N-(3-(trifluoromethyl)phenyl)-2-hydroxy-5-chlorophenylacetic amide, N-(3-(trifluoromethyl)phenyl)-N'-(2-hydroxy-5-chlorophenyl) thiourea, N-(3-(trifluoromethyl)phenyl)-N'-(2-hydroxy-5-methoxycarbonylphenyl) urea,
N-(3-(trifluoromethyl)phenyl)-N'-(2-hydroxy-4-nitro-5-carboxyphenyl) urea,
N-(3-(trifluoromethyl)phenyl)-N'-(2-hydroxy-4-nitro-5-methoxycarbonylphenyl) urea,
N-(3-(trifluoromethyl)phenyl)-N'-(2-hydroxy-4-methoxycarbonyl-5-chlorophenyl) urea,
N-(3-(trifluoromethyl)phenyl)-N'-(2-hydroxy-4-methoxcarbonylphenyl) urea,
N-(3-(trifluoromethyl)phenyl)-N'-(2-hydroxy-4-chlorophenyl) urea,
N-(3-(trifluoromethyl)phenyl)-N'-(2-hydroxy-6-methoxy-3-pyridyl) urea,
N-(3-(trifluoromethyl)phenyl)-N'-(2-hydroxy-5-chloro-3-pyridyl) urea,
N-(3-(trifluoromethyl)phenyl)-N'-(2-hydroxy-3-nitrophenyl) urea,
N-(3-(trifluoromethyl)phenyl)-N'-(2-hydroxy-5-chloro-4-nitrophenyl) urea,
N-(3-(trifluoromethyl)phenyl)-N'-(2-hydroxy-4-methoxyphenyl) urea,
N-(3-(trifluoromethyl)phenyl)-N'-(2,4-dihydroxyphenyl) urea,
N-(3-(trifluoromethyl)phenyl)-N'-(2-hydroxy-5-methoxy-4-nitrophenyl) urea,
N-(3-(trifluoromethyl)phenyl)-N'-(2-hydroxy-5-nitrophenyl) urea,
N-(3-(trifluoromethyl)phenyl)-N'-(3-hydroxy-2-naphthyl) urea,
N-(3-(trifluoromethyl)phenyl)-N'-(3-hydroxy-2-pyridyl) urea,
N-(3-(trifluoromethyl)phenyl)-N'-(2-hydroxy-1-naphthyl) urea,
N-(3-(trifluoromethyl)phenyl)-N'-(2-hydroxy-5-chlorophenyl) urea,
N-(3-(trifluoromethyl)phenyl)-N'-(2-hydroxy-5-tert-butylphenyl) urea,
N-(3-(trifluoromethyl)phenyl)-N'-(2-hydroxy-5-methoxyphenyl) urea,
N-(3-(trifluoromethyl)phenyl)-N'-(2-hydroxy-4-nitrophenyl) urea,
N-(3-(trifluoromethyl)phenyl)-N'-(2-hydroxy-5-(trifluoromethyl)phenyl) urea,
N-(3-(trifluoromethyl)phenyl)-N'-(2-hydroxy-4-aminophenyl) urea,
N-(3-(trifluoromethyl)phenyl)-N'-(2-hydroxy-4-(phenylamino)phenyl) urea,
N-(3-(trifluoromethyl)phenyl)-N'-(2, 5-dihydroxyphenyl) urea,
N-(3-benzoyl)-N'-(2-hydroxy-5-chlorophenyl) urea,
N-(3-carbamoylphenyl)-N'-(2-hydroxy-5-chlorophenyl) urea,
N-(3-carboxyphenyl)-N'-(2-hydroxy-5-chlorophenyl) urea,
N-(3-hydroxyphenyl)-N'-(2-hydroxy-5-chlorophenyl) urea,
N-(3-methoxycarbonylphenyl)-N'-(2-hydroxy-5-chlorophenyl) urea,
N-(3-methylphenyl)-N'-(2-hydroxy-5-chlorophenyl) urea, or
N-(3-nitrophenyl)-N'-(2-hydroxy-5-chlorophenyl) urea, and
a method of preparing a compound as first above, comprising the step of a) reacting a compound having the formula

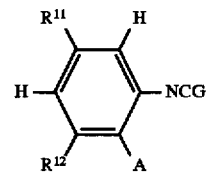

wherein A, $R^{11}$ and $R^{12}$ have the meanings set forth in claim 1, and G is O or S with a compound having the formula

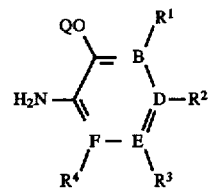

wherein B, D, E, F, $R^1$, $R^2$, $R^3$ and $R^4$ have the meanings set forth in claim 1 and Q is H or CH$_3$ as necessary, followed by deprotection with BBr$_3$ in case Q is CH$_3$, or b) reacting a compound having the formula

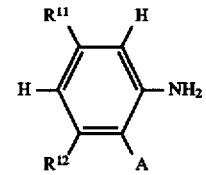

wherein A, $R^{11}$ and $R^{12}$ have the meanings set forth in claim 1, with a compound having the formula

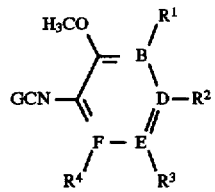

wherein B, D, E, F, $R^1$, $R^2$, $R^3$ and $R^4$ have the meanings set forth in claim 1, and G is O or S followed by deprotection with BBr$_3$, or c) reacting a compound having the formula

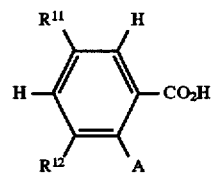

wherein A, $R^{11}$ and $R^{12}$ have the meanings set forth in claim 1 with a compound having the formula

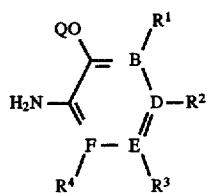

wherein B, D, E, F, R¹, R², R³ and R⁴ have the meanings set forth in claim 1, using dicyctohexylcarbodiimide as coupling agent followed by deprotection with BBr₃, or d) reacting a compound having the formula

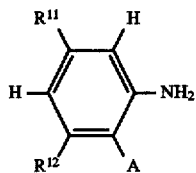

wherein A, R¹¹ and R¹² have the meanings set forth in claim 1 with a compound having the formula

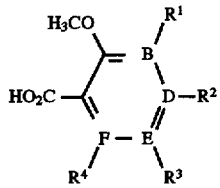

wherein B, D, E, F, R¹, R², R³ and R⁴ have the meanings set forth in claim 1 using dicyclohexylcarbodiimide as coupling agent followed by deprotection with BBr₃, or e) reacting a compound having the formula

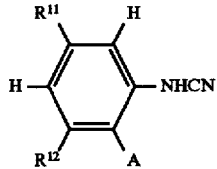

wherein A, R¹¹ and R¹² have the meanings set forth in claim 1 with a compound having the formula

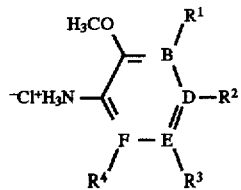

wherein B, D, E, F, R¹, R², R³ and R⁴ have the meanings set forth in claim 1 followed by deprotection with BBr₃, or f) reacting a compound having the formula

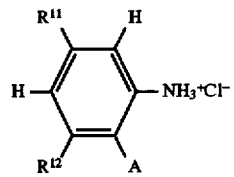

wherein A, R¹¹ and R¹² have the meanings set forth in claim 1 with a compound having the formula

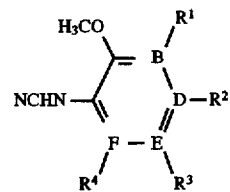

wherein B, D, E, F, R¹, R², R³ and R⁴ have the meanings set forth in claim 1 followed by deprotection with BBr₃, or g) reacting a compound having the formula

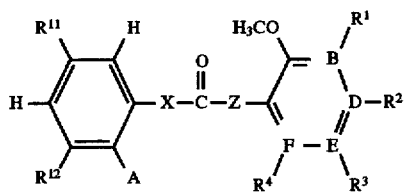

wherein X, Z, A, B, D, E, F, R¹, R², R³, R⁴, R¹¹ and R¹² have the meanings set forth in claim 1 with Lawesson's Reagent or P₂S₅ followed by deprotection with BBr₃, and a method as above wherein N-(2-hydroxy-5-chlorophenyl)-3-(trifluoromethyl) phenylacetic amide, N-(3-(trifluoromethoxy)phenyl)-N'-(2-hydroxy-5-chlorophenyl) urea, N-(3-(trifluoromethyl)phenyl)-N'-(2-hydroxyphenyl) urea, N-(3-(trifluoromethyl)phenyl)-N'-(2-hydroxy-6-nitrophenyl) urea, N-(3-(trifluoromethyl)phenyl)-2-hydroxy-5-chlorophenylacetic amide, N-(3-(trifluoromethyl)phenyl)-N'-(2-hydroxy-5-chlorophenyl) thiourea, N-(3-(trifluoromethyl)phenyl)-N'-(2-hydroxy-5-methoxycarbonylphenyl) urea, N-(3-(trifluoromethyl)phenyl)-N'-(2-hydroxy-4-methoxycarbonyl-5-chlorophenyl) urea, N-(3-(trifluoromethyl)phenyl)-N'-(2-hydroxy-4-methoxcarbonylphenyl) urea, N-(3-(trifluoromethyl)phenyl)-N'-(2-hydroxy-4-chlorophenyl) urea, N-(3-(trifluoromethyl)phenyl)-N'-(2-hydroxy-6-methoxy-3-pyridyl) urea, N-(3-(trifluoromethyl)phenyl)-N'-(2-hydroxy-5-chloro-3-pyridyl) urea, N-(3-(trifluoromethyl)phenyl)-N'-(2-hydroxy-3-nitrophenyl) urea, N-(3-(trifluoromethyl)phenyl)-N'-(2-hydroxy-4-methoxyphenyl) urea, N-(3-(trifluoromethyl)phenyl)-N'-(2,4-dihydroxyphenyl) urea, N-(3-(trifluoromethyl)phenyl)-N'-(2-hydroxy-5-nitrophenyl) urea, N-(3-(trifluoromethyl)phenyl)-N'-(3-hydroxy-2-naphthyl) urea, N-(3-(trifluoromethyl)phenyl)-N'-(3-hydroxy-2-pyridyl) urea, N-(3-(trifluoromethyl)phenyl)-N'-(2-hydroxy-1-naphthyl) urea, N-(3-(trifluoromethyl)phenyl)-N'-(2-hydroxy-5-chlorophenyl) urea, N-(3-(trifluoromethyl)phenyl)-N'-(2-hydroxy-5-methoxyphenyl) urea, N-(3-(trifluoromethyl)phenyl)-N'-(2,5-dihydroxyphenyl) urea, N-(3-benzoylphenyl)-N'-(2-hydroxy-5-chlorophenyl) urea, N-(3-carbamoylphenyl)-N'-(2-hydroxy-5-chlorophenyl) urea, N-(3-carboxyphenyl)-N'-(2-hydroxy-5-chlorophenyl) urea, N-(3-hydroxyphenyl)-N'-(2-hydroxy-5-chlorophenyl) urea, N-(3-methoxycarbonylphenyl)-N'-(2-hydroxy-5-chlorophenyl) urea, N-(3-methylphenyl)-N'-(2-hydroxy-5-chlorophenyl) urea, or N-(3-nitrophenyl)-N'-(2-hydroxy-5-chlorophenyl) urea, is prepared.

Halogen is fluorine, chlorine, bromine, or iodine.

Alkyl means a straight chained or branched chain of from one to six carbon atoms, cyclic alkyl of from three to seven carbon atoms, or cycloalkylalkyl, including but not limited to, methyl, ethyl, propyl, isopropyl, butyl, isobutyl, t-butyl, pentyl, hexyl, cyclopropyl, cyclobutyl, cyclopentyl, cyclohexyl, cyclopropylmethyl; methyl, ethyl, propyl and isopropyl are preferred groups.

Alkoxy means O-alkyl, wherein alkyl is as defined above.

Acyl means (C=O)-alkyl wherein alkyl is as defined above.

Amino means $NH_2$ or NH-alkyl, N-(alkyl)$_2$, NH-acyl, NH-phenyl or N(acyl)$_2$.

Sulphamoyl means $SO_2$-amino, wherein amino is as defined above.

Examples of pharmaceutically-acceptable addition salts include inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate. Such salts are formed by procedures well known in the art.

Other acids such as oxalic acid, while not in themselves pharmaceutically acceptable may be useful in the preparation of salts useful as intermediates in obtaining compounds of the invention and their pharmaceutically acceptable acid addition salts.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention exist in (+) and (−) forms as well as in racemic forms. Racemic forms can be resolved into the optical antipodes by known methods, for example, by separation of diastereomeric salts thereof, with an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallization of d- or l- (tartrates, mendelates, or camphorsulphonate) salts for example.

The compounds of the present invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolvation of optical isomers, known to those skilled in the art may be used, and will be apparent to the average skilled in the art. Such methods include those discussed by J. Jaques, A. Collet, and S. Wilen in "Enantiomers, Racemates, and Resolutions", John Wiley and Sons, New York (1981).

Starting materials for the processes described in the present application are known or can be prepared by known processes from commercially available chemicals.

The products of the reactions described herein are isolated by conventional means such as extraction, crystallization, distillation, chromatography, and the like.

Biology

The compounds of the present invention are potent openers of the high conductance BK channel, and the ability of the compounds of the present invention to open the BK channel can be demonstrated in several ways.

All experiments were performed with patch-clamp technique (Hamill et al., Pflügers Arch. 391, 85–100 (1981)). The ion composition of the internal solution was (in mM) 140 KCl, 1 $CaCl_2$, 1 $MgCl_2$, 2 EGTA, 10 HEPES and the external solution contained 140 NaCl, 4 KCl, 2 $CaCl_2$, 1 $MgCl_2$ and 10 HEPES.

Whole Cell Recordings

The membrane currents of calf aortic smooth muscle cells were determined in whole-cell recordings using voltage clamp mode (HEKA EPC-9 patch-clamp amplifier). Administration of N-(3-(trifluoromethyl)phenyl)-N'-(2-hydroxy-5-chlorophenyl) urea to the bath at concentrations of 1–10 μM specifically activated BK currents, which were blockable by charybdotoxin, by increasing the outward current by up to 10 times and shifting the activation curve by more than −60 mV towards negative membrane potentials.

A selective activation of BK currents was also found in cultured cortical neurons, cerebellar granule cells, PC12 cells and in human coronary artery smooth muscle cells. No effect was found on $Na^+$ currents or voltage-dependent $K^+$ currents (A type, delayed rectifier type) also present in the neuronal cells.

Single Channel Experiments

In inside-out patches of human coronary artery smooth muscle cell membrane single BK channels were activated by for example N-(3-(trifluoromethyl)phenyl)-N'-(2-hydroxy-5-chlorophenyl) urea (1–10 μM). This compound increased the open probability of the BK channel with several hundred percent.

Likewise in cultured bovine aortic smooth muscle cells in which the BK channel is the predominant $K^+$ channel for example N-(3-(trifluoromethyl)phenyl)-N'-(2-hydroxy-5-chlorophenyl) urea (1 μM) significantly activated the BK channel. The BK channels were also activated by N-(3-(trifluoromethyl)phenyl)-N'-(2-hydroxy-5-chlorophenyl) urea and N-phenyl-N'-(2-hydroxy-5-chlorophenyl) urea at concentrations equal or greater than 3 µM and by N-(3-(trifluoromethyl)phenyl)-N'-(2-hydroxy-5-(trifluoromethyl) phenyl) urea at concentrations greater than 10 µM.

Guinea-Pig Ileum Experiment

The compound, N-(3-(trifluoromethyl)phenyl)-N'-(2-hydroxy-5-chlorophenyl) urea, has been studied for its ability to relax acetylcholine-contracted guinea-pig ileum. The smooth muscle cells of the ileum express many BK channels and the model predicts relaxing effects on the gastrointestinal or urogenital tracts. The above mentioned compound relaxes the ileum in a dose-dependent way (3–30 µM).

Method: Ileum from guinea-pigs are isolated and mounted in an isometric contraction chamber. It is bathed in a physiological Krebs solution at 98° F. The ileum is precontracted with increasing concentrations of acetylcholine (0.015–5.0 µM). The contractions are reversed by including the compound in the bathing solution.

Cocaine Experiment

The compound, N-(3-(trifluoromethyl)phenyl)-N'-(2-hydroxy-5-chlorophenyl) urea, has been studied in the cocaine motility test. Cocaine induces hypermotility due to an inhibition of dopamine reuptake. The test is recognized as a test predicting anti-psychotic activity. The above mentioned compound (10–30 mg/kg) antagonizes cocaine induced hypermotility according to the test procedure described below.

Method: Two female NMRI mice (20–25 g) are placed in each test box (normal transparent plexiglas cage, w, l, h=21×39×19 cm) in the test room for at least 16 hours with food and water ad libitum before the test in order for the animals to habituate to the situation. The test compound is administered i.p. 15 min before saline or 25 mg/kg cocaine jip. to 32 mice (16 boxes) per dose. Food and water are withdrawn, and the motility is measured as the number of interrupted infrared photo-beams (8 per box placed 5 cm apart and 3 cm over the bottom of the cage) for the next 120 min.

These results also demonstrate that the compounds of the invention are potential anti-psychotics acting by a novel discovered mechanism.

Pharmaceutical Compositions

While it is possible that, for use in therapy, a compound of the invention may be administered as the raw chemical, then it is preferable to present the active ingredient as a pharmaceutical formulation.

The invention thus further provides a pharmaceutical formulation comprising a compound of the invention or a pharmaceutically acceptable salt or derivative thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting vax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting vax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pressaries, tampons, creams, gels, pastes, foams or sprays containing, in addition to the active ingredient, such carriers as are known in the art to be appropriate.

Liquid form preparations include solutions, suspensions, and emulsions, for example, water or water propylene glycol solutions. For example, parenteral injection liquid preparations can be formulated in solutions in aqueous polyethylene glycol solution.

The compounds according to the present invention may thus be formulated for parenteral administration (e.g. by injection, for example bolus injection or continuous infusion) and may be presented in unit dose form in ampoules, prefilled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and, in general, will also contain one or more emulsifying agents, stabilizing agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasel cavity by conventional means, for example with a dropper, pipette or spray. The formulations may be provided in single or multidose form. In the latter case of a dropper or pipette this may be achieved by the patient administering an appropriate, predetermined volume of the solution of suspension. In the case of a spray this may be achieved for example by means of a metering atomizing spray pump.

Administration to the respiratory tract may also be achieved by means of an aerosol formulation in which the active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidine (PVP). Conveniently the powder carrier will form a gel in the nasal cavity. The powder composition may be presented in unit dose form for example in capsules or cartridges of e.g. gelatin or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Method of Treating

The compounds of this invention are extremely useful in the treatment of disorders or diseases of mammals due to their potent potassium channel activating properties. These properties make the compounds of this invention extremely useful in the treatment of potassium channel dependent convulsions, potassium channel dependent asthma, potassium channel dependent arterial hypertension, potassium channel dependent coronary artery spasms, potassium channel dependent irritable bowl, potassium channel dependent spastic bladder, potassium channel dependent ischemia, and other disorders sensitive to potassium channel activating activity. The compounds of this invention may accordingly be administered to a subject, including a human, in need of treatment, alleviation, or elimination of an indication associated with the potassium channels. This includes especially convulsions and every form of epilepsia, asthma, hypertension, spastic bladder, irritable bowl, coronary artery spasms, aterial hypertension, psychosis and ischemia.

Suitable dosage range are 0.1–1000 milligrams daily, 10–500 milligrams daily, and especially 30–100 milligrams daily, dependent as usual upon the exact mode of administration, form in which administered, the indication toward which the administration is directed, the subject involved and the body weight of the subject involved, and further the preference and experience of the physician or veterinarian in charge.

The following examples will illustrate the invention further, however, they are not to be construed as limiting.

EXAMPLE 1

N-(3-(trifluoromethyl)phenyl)-N'-(2-hydroxy-5-nitrophenyl) urea 2-hydroxy-5-nitroaniline (1.25 g, 8.1 mmol) and 3-(trifluoromethyl)phenyl isocyanate (1.00 ml, 7.3 mmol)

were added to toluene (50 ml). The reaction mixture was stirred at RT overnight, the product filtered off and recrystallized from methanol/water 8:1 (45 ml).

1.39 g (56%) of the title compound was isolated. M.p. 226° C. (dec.).

The following compounds were prepared in a similar manner.

N-(3-(trifluoromethyl)phenyl)-N'-(2,5-dimethoxyphenyl) urea,
N-(3-(trifluoromethyl)phenyl)-N'-(2-methoxy-5-(phenylamino)phenyl) urea,
N-(3-(trifluoromethyl)phenyl)-N'-(2-hydroxy-4-nitrophenyl) urea. M.p. 199°–200° C.,
N-(3-(trifluoromethyl)phenyl)-N'-(2-hydroxy-5-chlorophenyl) urea. M.p. 171°–173° C.,
N-(3-(trifluoromethyl)phenyl)-N'-(2-hydroxy-5-tert-butylphenyl) urea. M.p. 173°–174° C.,
N-(3-(trifluoromethyl)phenyl)-N'-(2-hydroxy-5-methoxyphenyl) urea. M.p. 153°–154° C.,
N-(3-(trifluoromethyl)phenyl)-N'-(2-methoxy-5-(trifluoromethyl)phenyl) urea. M.p. 192°–194°C.,
N-(3-(trifluoromethyl)phenyl)-N'-(3-hydroxy-2-naphthyl) urea. M.p. 184°–188° C. (dec.),
N-(3-(trifluoromethyl)phenyl)-N'-(3-hydroxyl-2-pyridyl) urea. M.p. 181°–183° C.,
N-(3-(trifluoromethyl)phenyl)-N'-(2-hydroxy-1-naphthyl) urea. M.p. 187°–189° C. (dec),
N-(3-(trifluoromethyl)phenyl)-N'-(2-methoxy-5-chlorophenyl) urea. M.p. 169°–171° C.,
N-(3-(trifluoromethyl)phenyl)-N'-(2-hydroxy-6-nitrophenyl) urea. M.p. 174°–175° C.,
N-(3-(trifluoromethyl)phenyl)-N'-(2-hydroxyphenyl) urea. M.p. 178°–179° C.,
N-(3-(trifluoromethyl)phenyl)-N'-(2, 5-dimethoxy-4-nitrophenyl) urea,
N-(3-(trifluoromethyl)phenyl)-N'-(2-hydroxy-4-methoxcarbonylphenyl) urea. M.p. 222°–223° C.,
N-(3-(trifluoromethyl)phenyl)-N'-(2-hydroxy-3-nitrophenyl) urea. M.p. 223°–224° C.,
N-(3-(trifluoromethyl)phenyl)-N'-(2,6-dimethoxy-3-pyridyl) urea,
N-(3-(trifluoromethyl)phenyl)-N'-(2-hydroxy-5-chloro-3-pyridyl) urea. M.p. >310° C.,
N-(3-(trifluoromethyl)phenyl)-N'-(2-hydroxy-4-chlorophenyl) urea. M.p. 173°–174° C.,
N-(3-(trifluoromethyl)phenyl)-N'-(2-methoxy-5-methoxycarbonyl-4-nitrophenyl) urea,
N-(3-(trifluoromethyl)phenyl)-N'-(2-hydroxy-5-chloro-4-nitrophenyl) urea. M.p. 201°–203° C.,
N-(3-(trifluoromethyl)phenyl)-N'-(2-hydroxy-4-methoxycarbonyl-5-chlorophenyl) urea. M.p. 173°–174° C.,
N-(3-(trifluoromethyl)phenyl)-N'-(2-methoxy-5-methoxycarbonylphenyl) urea,
N-(3-(trifluoromethyl)phenyl)-N'-(2-methoxy-4-nitro-5-carboxyphenyl) urea.

EXAMPLE 2

N-(3-(trifluoromethyl)phenyl)-N'-(2-hydroxy-4-aminophenyl) urea.

N-(3-(trifluoromethyl)phenyl)-N'-(2-hydroxy-4-nitrophenyl) urea (1.00 g, 2.9 mmol) was subjected to catalytic reduction in tetrahydrofuran (50 ml) using 5% palladium on carbon (0.20 g). The reaction mixture was filtered through a path of celite. Evaporation of the filtrate and subsequent recrystallization of the crude product from methanol/water 1:1 (50 ml) afforded the title compound. 0.68 g (75%) of the title compound was isolated. M.p. 200°–202° C.

EXAMPLE 3

N-(1-naphthyl)-N'-(2-hydroxy-5-(trifluoromethyl) phenyl) urea.

2-hydroxy-5-(trifluoromethyl)aniline (0.12 g, 0.7 mmol) in toluene (3 ml) was added to a solution of alpha-naphthyl isocyanate (0.11 g, 0.7 mmol) in toluene (3 ml). The reaction was stirred at RT overnight and the product filtered off. 0.17 g (72%) of the title compound was isolated. M.p. 205°–207° C.

EXAMPLE 4

N-(2-methoxy-5-chlorophenyl)-3-(trifluoromethyl) phenylacetic amide.

Dicyclohexylcarbodiimide (2.20 g, 10.7 mmol) was added to a solution of 3-(trifluoromethyl)phenylacetic acid (2.00 g, 9.8 mmol) and 5-chloro-2-methoxyaniline (1.55 g, 9.8 mmol) in dichloromethane (50 ml). The reaction was stirred at RT overnight. The reaction mixture was filtered and the filtrate evaporated to dryness. The residue was recrystallized from methanol/water 2:1 (30 ml). 2.05 g (61%) of the title compound was isolated.

The following compound was prepared in a similar manner.

N-(3-(trifluoromethyl)phenyl)-2-methoxy-5-chlorophenylacetic amide starting from 3-trifluoromethylphenylamine and 2-methoxy-5-chlorophenylacetic acid.

EXAMPLE 5

N-(3,5-dichlorophenyl)-N'-(2-methoxy-5-(trifluoromethyl)phenyl) urea 3,5-dichlorophenyl isocyanate (0.94 g, 5.0 mmol) in toluene (10 ml) was added to a solution of 2-methoxy-5-(trifluoromethyl)aniline (0.96 g, 5.0 mmol) in toluene (10 ml). The reaction was stirred at RT for 1 hour and the product filtered off. 1.20 (63%) of the title compound was isolated.

EXAMPLE 6

N-(5,6,7,8-tetrahydro-1-naphthyl)-N'-(2-methoxy-5-(trifluoromethyl)phenyl) urea.

2-methoxy-5-(trifluoromethyl)phenyl carbamoylchloride (0.81 g, 3.2 mmol), 1-amino-5,6,7,8-tetrahydronaphtalene (445 µl, 3.2 mmol) and triethylamine (446 µl, 3.2 mmol) were added to chloroform (20 ml) and the resulting mixture was stirred at RT overnight. The reaction mixture was poured into water and extracted with ethyl acetate. The solvent was evaporated in vacuo and the residue recrystallized from toluene (20 ml). 0.45 g of the title compound was isolated.

EXAMPLE 7

N-(3-(trifluoromethyl)phenyl)-N'-(2-methoxy-5-(trifluoromethyl)phenyl) thiourea.

3-(trifluoromethyl)phenyl isothiocyanate in toluene (0.76 ml, 5.0 mmol) was added to a solution of 2-methoxy-5-(trifluoromethyl)aniline in toluene (10 ml). The resulting reaction mixture was stirred at RT overnight and the product was subsequently filtered off. 1.00 g (51%) of the title compound was isolated.

The following compound was prepared in a similar manner. N-(3-(trifluoromethyl)phenyl)'-N'-(2-methoxy-5-chlorophenyl) thiourea.

EXAMPLE 8

N-(3-methoxycarbonylphenyl)-N'-(2-methoxy-5-chlorophenyl) urea.

N-(3-carboxyphenyl)-N'-(2-methoxy-5-chlorophenyl) urea (3.00 g, 9.4 mmol) was suspended in methanol (100 ml). Concentrated sulfuric acid (1.0 ml) was added and the reaction was heated at reflux for 6 hours. The reaction mixture was poured into cold (0° C.) water (600 ml). Filtration of the suspension afforded the crude product. The crude product was purified by column chromatography on silica using dichloromethane/ethyl acetate 19:1 as eluent. 2.35 g of the title compound was isolated.

EXAMPLE 9

1-(3-(trifluoromethyl)phenyl-3-(2-methoxy-5-chlorophenyl) guanidine.

A mixture of 3-(trifluoromethyl)phenylcyanamide (2.00 g, 10.7 mmol) and 5-chloro-2-methoxyaniline hydrochloride (2.30 g, 11.8 mmol) was suspended in acetonitrile (80 ml). The reaction was heated at reflux for four days. The solvent was evaporated in vacuo. The residue was redissolved in dichloromethane (100 ml) and washed with a saturated sodium bicarbonate solution. The crude product was purified by column chromatography on silica gel initially using dichloromethane as eluent followed by dichloromethane/methanol 9:1 as eluent. 2.27 g of the title compound was obtained as a dark oil which slowly crystallises.

EXAMPLE 10

N-(3-benzoylphenyl)-N'-(2-methoxy-5-chlorophenyl) urea.

A mixture of 5-chloro-2-methoxyphenyl isocyanate (1.00 g, 5.4 mmol) and 3-aminobenzophenone (1.29 g, 6.5 mmol) was stirred in toluene (20 ml) for two days. The reaction was filtered and the filter cake washed with toluene. 1.9 g of the title compound was isolated.

The following compounds were prepared in a similar manner.

N-(3-carbamoylphenyl)-N'-(2-methoxy-5-chlorophenyl) urea,
N-(3-(trifluoromethoxy)phenyl)-N'-(2-methoxy-5-chlorophenyl) urea,
N-(3-methylphenyl)-N'-(2-methoxy-5-chlorophenyl) urea,
N-(3-hydroxyphenyl)-N'-(2-methoxy-5-chlorophenyl) urea,
N-(3-nitrophenyl)-N'-(2-methoxy-5-chlorophenyl) urea, and
N-(3-carboxyphenyl)-N'-(2-methoxy-5-chlorophenyl) urea.

EXAMPLE 11

N-(3-(trifluoromethyl)phenyl)-N'-(2-hydroxy-5-(phenylamino)phenyl) urea

To a cold (0° C.) suspension of N-(3-(trifluoromethyl)phenyl)-N'-(2-methoxy-5-(phenylamino)phenyl) urea (1.00 g, 2.5 mmol) in dichloromethane (50 ml), boron tribromide (0.48 ml, 5.1 mmol) was added. After the addition of boron tribromide the ice bath was removed and the reaction mixture was stirred for 3 hours at RT. The reaction was poured on ice (10 ml) and 1M sodium bicarbonate (50 ml) was added. The aqueous phase was extracted with ethyl acetate (50 ml) and the organic phase dried over magnesium sulfate. 1.05 g crude product was obtained. The crude product was purified by column chromatography on silica gel using petroleum ether/ethyl acetate 1:1 as eluent. The partly purified product (0.61 g) was recrystallized from ethanol/water 1:1 (20 ml). 0.20 g (21%) of the title compound was isolated. M.p. 166°–168° C.

The following compounds were prepared in a similar manner.

N-(3-(trifluoromethyl)phenyl)-N'-(2, 5-dihydroxyphenyl) urea, M.p. 165°–168° C.,
N-(3-(trifluoromethyl)phenyl)-N'-(2-hydroxy-5-(trifluoromethyl)phenyl) urea, M.p. 160°–162° C.,
N-(3-(trifluoromethyl)phenyl)-N'-(2-hydroxy-5-chlorobenzyl) urea, M.p. 56°–66° C.,
N-(3-(trifluoromethyl)phenyl)-N'-(2,3-dihydroxybenzyl) urea, M.p. 159°–161° C.,
N-(2-hydroxy-5-chlorophenyl)-3-(trifluoromethyl) phenylacetic amide, M.p. 148°–153° C.,
N-(3,5-dichlorophenyl)-N'-(2-hydroxy-5-(trifluoromethyl)phenyl) urea, M.p. 202° C.,
N-(5,6,7,8-tetrahydro-1-naphthyl)-N'-(2-hydroxy-5-(trifluoromethyl)phenyl) urea,
N-(3-(trifluoromethyl)phenyl)-N'-(2-hydroxy-5-(trifluoromethyl)phenyl) thiourea, M.p. 124°–125° C.,
N-(3-methylphenyl)-N'-(2-hydroxy-5-chlorophenyl) urea, M.p. 179°–180° C.,
N-(3-hydroxyphenyl)-N'-(2-hydroxy-5-chlorophenyl) urea,
N-(3-nitrophenyl)-N'-(2-hydroxy-5-chlorophenyl) urea, M.p. 194°–196° C.,
N-(3-carboxyphenyl)-N'-(2-hydroxy-5-chlorophenyl) urea, M.p. 216° C.,
N-(3-benzoylphenyl)-N'-(2-hydroxy-5-chlorophenyl) urea, M.p. 205°–206° C.,
N-(3-carbamoylphenyl)-N'-(2-hydroxy-5-chlorophenyl) urea, M.p. 203°–204° C.,
N-(3-(trifluoromethoxy)phenyl)-N'-(2-hydroxy-5-chlorophenyl) urea, M.p. 158°–159° C.,
N-(3-(trifluoromethyl)phenyl)-N'-(2-hydroxy-5-methoxy-4-nitrophenyl) urea, M.p. 220°–222° C.,
N-(3-methoxycarbonylphenyl)-N'-(2-hydroxy-5-chlorophenyl) urea, M.p. 182° C.,
N-(3-(trifluoromethyl)phenyl)-N'-(2,4-dihydroxyphenyl) urea, M.p. 179°–180° C.,
N-(3-(trifluoromethyl)phenyl)-N'-(2-hydroxy-4-methoxyphenyl) urea, M.p. 176°–177° C.,
N-(3-(trifluoromethyl)phenyl)-N'-(2-hydroxy-6-methoxy-3-pyridyl) urea, M.p. 223°–224° C.,
N-(3-(trifluoromethyl)phenyl)-N'-(2-hydroxy-4-nitro-5-methoxycarbonylphenyl) urea, M.p. 201°–202° C.,
N-(3-(trifluoromethyl)phenyl)-N'-(2-hydroxy-5-methoxycarbonylphenyl) urea, M.p. 205°–206° C.,
N-(3-(trifluoromethyl)phenyl)-N'-(2-hydroxy-5-chlorophenyl) thiourea.
N-(3-(trifluoromethyl)phenyl)-N'-(2-hydroxy-4-nitro-5-carboxyphenyl) urea, M.p. 201°–203° C.,
1-(3-(trifluoromethyl)phenyl-3-(2-hydroxy-5-chlorophenyl) guanidine, M.p. 172°–174° C., and
N-(3-(trifluoromethyl)phenyl)-2-hydroxy-5-chlorophenylacetic amide, M.p. 148°–150° C.

We claim:
1. A compound having the formula

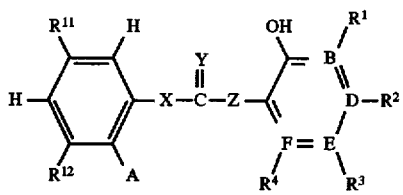

or a pharmaceutically acceptable salt thereof,
wherein

X is NH or $CH_2$, and Z is NH;

Y is O, S, NCN, or NH;

B,D,E and F each independently are C or N, at least three of B, D, E, and F being C;

$R^1$ and $R^4$ each independently are hydrogen, halogen, $CF_3$, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy;

$R^2$ is hydrogen, $CF_3$, COOH, COO-alkyl, COO-aryl, CO-amino, CN, alkoxy, hydroxy, hydroxymethyl, sulphamoyl, aryloxy, alkylcarbonyl, arylcarbonyl, arylcarbonyloxy, alkylcarbonyloxy;

$R^3$ is hydrogen, halogen, COOH, COO-alkyl, COO-aryl, CO-amino, CN, alkoxy, hydroxy, nitro, hydroxymethyl, sulphamoyl, amino, aryloxy, alkylcarbonyl, arylcarbonyl, arylcarbonyloxy, alkylcarbonyloxy; or $R^2$ and $R^3$ or $R^3$ and $R^4$ together with the carbon atoms to which they are attached form an additional fused carbocyclic ring which may be fully or partially unsaturated;

at least one of $R^{11}$ or $R^{12}$ is halogen, $OCF_3$, $CF_3$, COOH, COO-alkyl, COO-aryl, CO-amine, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy and the other of $R^{11}$ or $R^{12}$ is hydrogen, halogen, $OCF_3$, $CF_3$, COOH, COO-alkyl, COO-aryl, CO-amino, CN, alkyl, alkoxy, hydroxy, nitro, hydroxymethyl, sulphamoyl, amine, aryloxy, alkylcarbonyl, arylcarbonyl, arylcarbonyloxy, alkylcarbonyloxy;

A is hydrogen or together with $R^{12}$ and the carbon atoms to which they are attached form an additional fused carbocyclic ring which may be fully or partially unsaturated.

2. A compound of claim 1 which is

N-(2-hydroxy-5-chlorophenyl)-3-(trifluoromethyl)phenylacetic amide,

N-(3-(trifluoromethoxy)phenyl)-N'-(2-hydroxy-5-chlorophenyl) urea,

N-(3-(trifluoromethyl)phenyl)-N'-(2-hydroxyphenyl) urea,

N-(3-(trifluoromethyl)phenyl)-N'-(2-hydroxy-6-nitrophenyl) urea,

N-(3-(trifluoromethyl)phenyl)-N'-(2-hydroxy-5-chlorophenyl)thiourea,

N-(3-(trifluoromethyl)phenyl)-N'-(2-hydroxy-5-methoxycarbonylphenyl) urea,

N-(3-(trifluoromethyl)phenyl)-N'-(2-hydroxy-4-methoxycarbonyl-5-chlorophenyl) urea, N-(3-(trifluoromethyl)phenyl)-N'-(2-hydroxy-4-methoxcarbonylphenyl) urea, N-(3-(trifluoromethyl)phenyl)-N'-(2-hydroxy-4-chlorophenyl) urea, N-(3-(trifluoromethyl)phenyl)-N'-(2-hydroxy-6-methoxy-3-pyridyl) urea, N-(3-(trifluoromethyl)phenyl)-N'-(2-hydroxy-5-chloro-3-pyridyl) urea, N-(3-(trifluoromethyl)phenyl)-N'-(2-hydroxy-3-nitrophenyl) urea, N-(3-(trifluoromethyl)phenyl)-N'-(2-hydroxy-4-methoxyphenyl) urea, N-(3-(trifluoromethyl)phenyl)-N'-(2,4-dihydroxyphenyl) urea, N-(3-(trifluoromethyl)phenyl)-N'-(2-hydroxy-5-nitrophenyl) urea, N-(3-(trifluoromethyl)phenyl)-N'-(3-hydroxy-2-naphthyl) urea, N-(3-(trifluoromethyl)phenyl)-N'-(3-hydroxy-2-pyridyl) urea, N-(3-(trifluoromethyl)phenyl)-N'-(2-hydroxy-1-naphthyl) urea, N-(3-(trifluoromethyl)phenyl)-N'-(2-hydroxy-5-chlorophenyl) urea, N-(3-(trifluoromethyl)phenyl)-N'-(2-hydroxy-5-methoxyphenyl) urea, N-(3-(trifluoromethyl)phenyl)-N'-(2-hydroxy-4-(phenylamino)phenyl) urea, N-(3-(trifluoromethyl)phenyl)-N'-(2,5-dihydroxyphenyl) urea, N-(3-benzoylphenyl)-N'-(2-hydroxy-5-chlorophenyl) urea, N-(3-carbamoylphenyl)-N'-(2-hydroxy-5-chlorophenyl) urea, N-(3-carboxyphenyl)-N'-(2-hydroxy-5-chlorophenyl) urea, N-(3-hydroxyphenyl)-N'-(2-hydroxy-5-chlorophenyl) urea, N-(3-methoxycarbonylphenyl)-N'-(2-hydroxy-5-chlorophenyl) urea, N-(3-methylphenyl)-N'-(2-hydroxy-5-chlorophenyl) urea, or N-(3-nitrophenyl)-N'-(2-hydroxy-5-chlorophenyl) urea, or a pharmaceutically acceptable salt thereof.

3. A pharmacodynamic pharmaceutical composition comprising a potassium-channel-opening amount of a compound having the formula

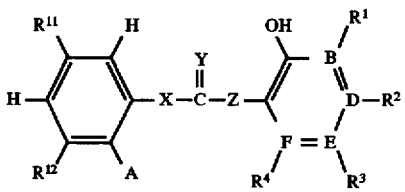

or a pharmaceutically acceptable salt thereof,
wherein

X and Z each independently are NH or $CH_2$, at least one of X and Z being NH;

Y is O, S, NCN, or NH;

B,D,E and F each independently are C or N, at least three of B, D, E, and F being C;

23

R¹ and R⁴ each independently are hydrogen, halogen, CF₃, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy;

R² is hydrogen, CF₃, COOH, COO-alkyl, COO-aryl, CO-amino, CN, alkoxy, hydroxy, hydroxymethyl, sulphamoyl, aryloxy, alkylcarbonyl, arylcarbonyl, arylcarbonyloxy, alkylcarbonyloxy;

R³ is hydrogen, halogen, COOH, COO-alkyl, COO-aryl, CO-amino, CN, alkoxy, hydroxy, nitro, hydroxymethyl, sulphamoyl, amino, aryloxy, alkylcarbonyl, arylcarbonyl, arylcarbonyloxy, alkylcarbonyloxy; or R² and R³ or R³ and R⁴ together with the carbon atoms to which they are attached form an additional fused carbocyclic ring which may be fully or partially unsaturated;

at least one of R¹¹ or R¹² is halogen, OCF₃, CF₃, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy and the other of R¹¹ or R¹² is hydrogen, halogen, OCF₃, CF₃, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy;

A is hydrogen or together with R¹² and the carbon atoms to which they are attached form an additional fused carbocyclic ring which may be fully or partially unsaturated;

together with at least one pharmaceutically acceptable carrier.

4. A method of treating a disorder or disease of a living animal body, which disorder or disease is responsive to opening of potassium channels and which comprises administering to such a living animal body, including a human in need thereof an effective amount of a compound having the formula

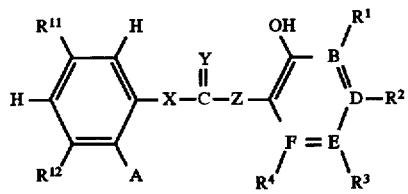

or a pharmaceutically acceptable salt thereof, wherein

X or Z each independently are NH or CH₂, at least one of X and Z being NH;

Y is O, S, NCN, or NH;

B,D,E and F each independently are C or N, at least three of B, D, E, and F being C;

R¹ and R⁴ each independently are hydrogen, halogen, CF₃, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, alcarbonyloxy, alkylcarbonyloxy;

R² is hydrogen, halogen, CF₃, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy;

24

R³ is hydrogen, halogen, CF₃, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy; or R² and R³ or R³ and R⁴ together with the carbon atoms to which they are attached form an additional fused carbocyclic ring which may be fully or partially unsaturated;

at least one of R¹¹ or R¹² is halogen, OCF₃, CF₃, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy and the other of R¹¹ or R² is hydrogen, halogen, OCF₃, CF₃, COOH, COO-alkyl, COO-aryl, CO-amino, CN, alkyl, alkoxy, hydroxy, nitro, hydroxymethyl, sulphamoyl, amino, aryloxy, alkylcarbonyl, arylcarbonyl, arylcarbonyloxy, alkylcarbonyloxy;

A is hydrogen or together with R¹² and the carbon atoms to which they are attached form an additional fused carbocyclic ring which may be fully or partially unsaturated.

5. The method of claim 4 wherein arterial hypertension, coronary artery spasms, asthma, irritable bowl syndrome, spastic bladder, ischemia, psychosis, or convulsions are treated.

6. The method of claim 4 wherein the compound is administered in the form of a pharmaceutical composition thereof, in which it is present together with a pharmaceutically acceptable carrier or diluent.

7. The method of claim 4 wherein

N-(1-naphthyl)-N'-(2-hydroxy-5-(trifluoromethyl) phenyl) urea,

N-(2-hydroxy-5-chlorophenyl)-3-(trifluoromethyl) phenylacetic amide,

N-(3,5-dichlorophenyl)-N'-(2-hydroxy-5-(trifluoromethyl)phenyl) urea,

N-(3-(trifluoromethoxy)phenyl)-N'-(2-hydroxy-5-chlorophenyl) urea,

N-(3-(trifluoromethyl)phenyl)-N'-(2-hydroxyphenyl) urea,

N-(3-(trifluoromethyl)phenyl)-N'-(2-hydroxy-6-nitrophenyl) urea,

N-(3-(trifluoromethyl)phenyl)-N'-(2-hydroxy-5-(trifluoromethyl)phenyl) thiourea, N-(3-(trifluoromethyl)phenyl)-2-hydroxy-5-chlorophenylacetic amide, N-(3-(trifluoromethyl)phenyl)-N'-(2-hydroxy-5-chlorophenyl) thiourea, N-(3-(trifluoromethyl)phenyl)-N'-(2-hydroxy-5-methoxycarbonylphenyl) urea, N-(3-(trifluoromethyl)phenyl)-N'-(2-hydroxy-4-nitro-5-carboxyphenyl) urea, N-(3-(trifluoromethyl)phenyl)-N'-(2-hydroxy-4-nitro-5-methoxycarbonylphenyl) urea, N-(3-(trifluoromethyl)phenyl)-N'-(2-hydroxy-4-methoxycarbonyl-5-chlorophenyl) urea, N-(3-(trifluoromethyl)phenyl)-N'-(2-hydroxy-4-methoxcarbonylphenyl) urea, N-(3-(trifluoromethyl)phenyl)-N'-(2-hydroxy-4-chlorophenyl) urea, N-(3-(trifluoromethyl)phenyl)-N'-(2-hydroxy-6-methoxy-3-pyridyl) urea, N-(3-(trifluoromethyl)phenyl)-N'-(2-hydroxy-5-chloro-3-pyridyl) urea,
N-(3-(trifluoromethyl)phenyl)-N'-(2-hydroxy-3-nitrophenyl) urea,
N-(3-(trifluoromethyl)phenyl)-N'-(2-hydroxy-5-chloro-4-nitrophenyl) urea,
N-(3-(trifluoromethyl)phenyl)-N'-(2-hydroxy-4-methoxyphenyl) urea,
N-(3-(trifluoromethyl)phenyl)-N'-(2,4-dihydroxyphenyl) urea,
N-(3-(trifluoromethyl)phenyl)-N'-(2-hydroxy-5-methoxy4-nitrophenyl) urea,
N-(3-(trifluoromethyl)phenyl)-N'-(2-hydroxy-5-nitrophenyl) urea,
N-(3-(trifluoromethyl)phenyl)-N'-(3-hydroxy-2-naphthyl) urea,
N-(3-(trifluoromethyl)phenyl)-N'-(3-hydroxy-2-pyridyl) urea,
N-(3-(trifluoromethyl)phenyl)-N'-(2-hydroxy-1-naphthyl) urea,
N-(3-(trifluoromethyl)phenyl)-N'-(2-hydroxy-5-chlorophenyl) urea,
N-(3-(trifluoromethyl)phenyl)-N'-(2-hydroxy-5-tert-butylphenyl) urea,
N-(3-(trifluoromethyl)phenyl)-N'-(2-hydroxy-5-methoxyphenyl) urea,
N-(3-(trifluoromethyl)phenyl)-N'-(2-hydroxy-4-nitrophenyl) urea,
N-(3-(trifluoromethyl)phenyl)-N'-(2-hydroxy-5-(trifluoromethyl)phenyl) urea,
N-(3-(trifluoromethyl)phenyl)-N'-(2-hydroxy-4-aminophenyl) urea,
N-(3-(trifluoromethyl)phenyl)-N'-(2-hydroxy-4-(phenylamino)phenyl) urea,
N-(3-(trifluoromethyl)phenyl)-N'-(2,5-dihydroxyphenyl) urea,
N-(3-benzoyl)-N'-(2-hydroxy-5-chlorophenyl) urea,
N-(3-carbamoylphenyl)-N'-(2-hydroxy-5-chlorophenyl) urea,
N-(3-carboxyphenyl)-N'-(2-hydroxy-5-chlorophenyl) urea,
N-(3-hydroxyphenyl)-N'-(2-hydroxy-5-chlorophenyl) urea,
N-(3-methoxycarbonylphenyl)-N'-(2-hydroxy-5-chlorophenyl) urea,
N-(3-methylphenyl)-N'-(2-hydroxy-5-chlorophenyl) urea, or
N-(3-nitrophenyl)-N'-(2-hydroxy-5-chlorophenyl) urea, is employed.

8. The pharmaceutical composition of claim 3 wherein the compound employed is
N-(1-naphthyl)-N'-(2-hydroxy-5-(trifluoromethyl)phenyl) urea,
N-(2-hydroxy-5-chlorophenyl)-3-(trifluoromethyl)phenylacetic amide,
N-(3,5-dichlorophenyl)-N'-(2-hydroxy-5-(trifluoromethyl)phenyl) urea,
N-(3-(trifluoromethoxy)phenyl)-N'-(2-hydroxy-5-chlorophenyl) urea,
N-(3-(trifluoromethyl)phenyl)-N'-(2-hydroxyphenyl) urea,
N-(3-(trifluoromethyl)phenyl)-N'-(2-hydroxy-6-nitrophenyl) urea,
N-(3-(trifluoromethyl)phenyl)-N'-(2-hydroxy-5-(trifluoromethyl)phenyl) thiourea,
N-(3-(trifluoromethyl)phenyl)-2-hydroxy-5-chlorophenylacetic amide,
N-(3-(trifluoromethyl)phenyl)-N'-(2-hydroxy-5-chlorophenyl) thiourea,
N-(3-(trifluoromethyl)phenyl)-N'-(2-hydroxy-5-methoxycarbonylphenyl) urea,
N-(3-(trifluoromethyl)phenyl)-N'-(2-hydroxy-4-nitro-5-carboxyphenyl) urea,
N-(3-(trifluoromethyl)phenyl)-N'-(2-hydroxy-4-nitro-5-methoxycarbonylphenyl) urea,
N-(3-(trifluoromethyl)phenyl)-N'-(2-hydroxy-4-methoxycarbonyl-5-chlorophenyl) urea,
N-(3-(trifluoromethyl)phenyl)-N'-(2-hydroxy-4-methoxcarbonylphenyl) urea,
N-(3-(trifluoromethyl)phenyl)-N'-(2-hydroxy-4-chlorophenyl) urea,
N-(3-(trifluoromethyl)phenyl)-N'-(2-hydroxy-6-methoxy-3-pyridyl) urea,
N-(3-(trifluoromethyl)phenyl)-N'-(2-hydroxy-5-chloro-3-pyridyl) urea,
N-(3-(trifluoromethyl)phenyl)-N'-(2-hydroxy-3-nitrophenyl) urea,
N-(3-(trifluoromethyl)phenyl)-N'-(2-hydroxy-5-chloro-4-nitrophenyl) urea,
N-(3-(trifluoromethyl)phenyl)-N'-(2-hydroxy-4-methoxyphenyl) urea,
N-(3-(trifluoromethyl)phenyl)-N'-(2,4-dihydroxyphenyl) urea,
N-(3-(trifluoromethyl)phenyl)-N'-(2-hydroxy-5-methoxy-4-nitrophenyl) urea,
N-(3-(trifluoromethyl)phenyl)-N'-(2-hydroxy-5-nitrophenyl) urea,
N-(3-(trifluoromethyl)phenyl)-N'-(3-hydroxy-2-naphthyl) urea,
N-(3-(trifluoromethyl)phenyl)-N'-(3-hydroxy-2-pyridyl) urea,
N-(3-(trifluoromethyl)phenyl)-N'-(2-hydroxy-1-naphthyl) urea,
N-(3-(trifluoromethyl)phenyl)-N'-(2-hydroxy-5-chlorophenyl) urea,
N-(3-(trifluoromethyl)phenyl)-N'-(2-hydroxy-5-tert-butylphenyl) urea,
N-(3-(trifluoromethyl)phenyl)-N'-(2-hydroxy-5-methoxyphenyl) urea,
N-(3-(trifluoromethyl)phenyl)-N'-(2-hydroxy-4-nitrophenyl) urea,
N-(3-(trifluoromethyl)phenyl)-N'-(2-hydroxy-5-(trifluoromethyl)phenyl) urea,
N-(3-(trifluoromethyl)phenyl)-N'-(2-hydroxy-4-aminophenyl) urea,
N-(3-(trifluoromethyl)phenyl)-N'-(2-hydroxy-4-(phenylamino)phenyl) urea,
N-(3-(trifluoromethyl)phenyl)-N'-(2,5-dihydroxyphenyl) urea,
N-(3-benzoyl)-N'-(2-hydroxy-5-chlorophenyl) urea, N-(3-carbamoylphenyl)-N'-(2-hydroxy-5-chlorophenyl) urea, N-(3-carboxyphenyl)-N'-(2-hydroxy-5-chlorophenyl) urea, N-(3-hydroxyphenyl)-N'-(2-hydroxy-5-chlorophenyl) urea, N-(3-methoxycarbonylphenyl)-N'-(2-hydroxy-5-chlorophenyl) urea, N-(3-methylphenyl)-N'-(2-hydroxy-5-chlorophenyl) urea, or N-(3-nitrophenyl)-N'-(2-hydroxy-5-chlorophenyl) urea.

* * * * *

UNITED STATES PATENT AND TRADEMARK OFFICE
CERTIFICATE OF CORRECTION

PATENT NO. : 5,696,138
DATED : Dec. 9, 1997
INVENTOR(S) : Seren-Peter Olesen; Peter Moldt, Ove Pedersen Page 1 of 4

It is certified that error appears in the above-indentified patent and that said Letters Patent is hereby corrected as shown below:

Title Page, [56] References Cited, Other Publications, Column 2, line 10: "Glybudrie" should read -- Glyburide --.

Title Page, [56] References Cited, Other Publications, Column 2, line 26: "J. Neurosci, 2(1)" should read -- J. Neurosci, 12(1) --.

Column 1, line 6: "1995." should read -- 1993. --

Column 4, line 33: "$R_{11}$" and $R_{12}$" should read -- $R^{11}$ and $R^{12}$ --.

Column 4, line 37: "$R_{11}$" and $R_{12}$" should read -- $R^{11}$ and $R^{12}$ --.

UNITED STATES PATENT AND TRADEMARK OFFICE
CERTIFICATE OF CORRECTION

PATENT NO. : 5,696,138
DATED : Dec. 9, 1997
INVENTOR(S) : Søren-Peter Olesen; Peter Moldt, Ove Pedersen Page 2 of 4

It is certified that error appears in the above-indentified patent and that said Letters Patent is hereby corrected as shown below:

Column 5, line 25: Insert the following missing page 8 of the SPECIFICATION:

-- N-(3-(trifluoromethyl)phenyl)-N'-(2-hydroxy-5-chloro-4-nitrophenyl) urea,

N-(3-(trifluoromethyl)phenyl)-N'-(2-hydroxy-4-methoxyphenyl) urea,

N-(3-(trifluoromethyl)phenyl)-N'-(2, 4-dihydroxyphenyl) urea,

N-(3-(trifluoromethyl)phenyl)-N'-(2-hydroxy-5-methoxy-4-nitrophenyl) urea,

N-(3-(trifluoromethyl)phenyl)-N'-(2-hydroxy-5-nitrophenyl) urea,

N-(3-(trifluoromethyl)phenyl)-N'-(3-hydroxy-2-naphthyl) urea,

N-(3-(trifluoromethyl)phenyl)-N'-(3-hydroxy-2-pyridyl) urea,

N-(3-(trifluoromethyl)phenyl)-N'-(2-hydroxy-1-naphthyl) urea,

N-(3-(trifluoromethyl)phenyl)-N'-(2-hydroxy-5-chlorophenyl) urea,

N-(3-(trifluoromethyl)phenyl)-N'-(2-hydroxy-5-tert-butylphenyl) urea,

N-(3-(trifluoromethyl)phenyl)-N'-(2-hydroxy-5-methoxyphenyl) urea,

N-(3-(trifluoromethyl)phenyl)-N'-(2-hydroxy-4-nitrophenyl) urea,

N-(3-(trifluoromethyl)phenyl)-N'-(2-hydroxy-5-(trifluoromethyl)phenyl) urea,

N-(3-(trifluoromethyl)phenyl)-N'-(2-hydroxy-4-aminophenyl) urea,

N-(3-(trifluoromethyl)phenyl)-N'-(2-hydroxy-4-(phenylamino)phenyl) urea,

N-(3-(trifluoromethyl)phenyl)-N'-(2, 5-dihydroxyphenyl) urea,

N-(3-benzoyl)-N'-(2-hydroxy-5-chlorophenyl) urea,

UNITED STATES PATENT AND TRADEMARK OFFICE
CERTIFICATE OF CORRECTION

PATENT NO. : 5,696,138
DATED : Dec. 9, 1997
INVENTOR(S) : Seren-Peter Olesen; Peter Moldt, Ove Pedersen It is certified that error appears in the above-indentified patent and that said Letters Patent is hereby corrected as shown below:

N-(3-carbamoylphenyl)-N'-(2-hydroxy-5-chlorophenyl) urea,

N-(3-carboxyphenyl)-N'-(2-hydroxy-5-chlorophenyl) urea,

N-(3-hydroxyphenyl)-N'-(2-hydroxy-5-chlorophenyl) urea,

N-(3-methoxycarbonylphenyl)-N'-(2-hydroxy-5-chlorophenyl) urea,

N-(3-methylphenyl)-N'-(2-hydroxy-5-chlorophenyl) urea, or

N-(3-nitrophenyl)-N'-(2-hydroxy-5-chlorophenyl) urea, is employed, and the use of a compound having the formula

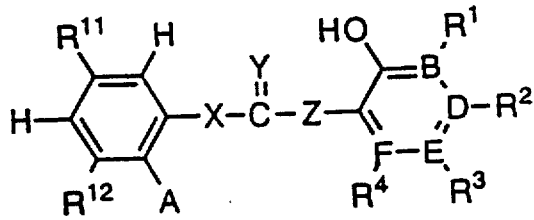

or a pharmaceutically acceptable salt thereof,    --

UNITED STATES PATENT AND TRADEMARK OFFICE
CERTIFICATE OF CORRECTION

PATENT NO.   : 5,696,138
DATED        : Dec. 9, 1997
INVENTOR(S)  : Seren-Peter Olesen; Peter Moldt, Ove Pedersen It is certified that error appears in the above-indentified patent and that said Letters Patent is hereby corrected as shown below:

Column 6, line 51: "5-(trifluorom ethyl)phenyl)" should read -- 5-(trifluoromethyl)phenyl) --.
Page 11, line 19.

Column 9, line 1-10 in the formula: "QO" at the top of the page should read --$H_3CO$ --. Page 14, line 7

Column 9, line 12(approx.): :dicyctohexylcarbodiimide" should read -- dicyclohexylcarbodiimide --.
Page 14, line 9

Column 13, line 39: "jip" at the beginning of the line should read -- i.p. --. Page 21, line 17

Column 23, line 62: "alcarbonyloxy;" should read -- arylcarbonyloxy --. "Substitute Claim Sheet".

Signed and Sealed this

Fourteenth Day of April, 1998

Attest:

BRUCE LEHMAN

Attesting Officer

Commissioner of Patents and Trademarks